United States Patent
Koch et al.

[11] Patent Number: 5,912,256
[45] Date of Patent: Jun. 15, 1999

[54] COMPOUNDS HAVING EFFECTS ON SEROTONIN-RELATED SYSTEMS

[75] Inventors: Daniel James Koch; Vincent Patrick Rocco, both of Indianapolis, Ind.

[73] Assignee: Eli Lilly and Company, Indianapolis, Ind.

[21] Appl. No.: 08/861,445

[22] Filed: May 22, 1997

Related U.S. Application Data

[60] Provisional application No. 60/020,131, Jun. 20, 1996.

[51] Int. Cl.$^6$ ............... A61K 31/445; A61K 31/495; C07D 401/14
[52] U.S. Cl. ............ 514/323; 514/253; 514/316; 544/364; 546/187; 546/201
[58] Field of Search .................... 546/187, 201; 544/364; 514/253, 316, 323

[56] References Cited

U.S. PATENT DOCUMENTS

| | | | |
|---|---|---|---|
| 5,013,761 | 5/1991 | Beedle et al. | 514/650 |
| 5,576,321 | 11/1996 | Krushinski et al. | 514/255 |
| 5,614,523 | 3/1997 | Audia et al. | 514/252 |
| 5,627,196 | 5/1997 | Audia et al. | 514/323 |

FOREIGN PATENT DOCUMENTS 0 722 941  7/1996  European Pat. Off. .

OTHER PUBLICATIONS

Rasmussen et al in "Recent Progress in Serotonin (5–HT)1A Receptor Modulators", Ann. Reports in Medicinal Chemistry. 30 pp. 1–9, 1995.

Saxena, *Pharmac. Ther.* vol. 66, pp. 339–368, 1995.

*Primary Examiner*—Emily Bernhardt
*Attorney, Agent, or Firm*—Nelsen L. Lentz; Arleen Palmberg

[57] ABSTRACT

A series of 1-(4-indolyloxy)-3-(4-hydroxy-4-naphthylpiperidin-1-yl)propanes are effective pharmaceuticals for the treatment of conditions related to or affected by the reuptake of serotonin and by the serotonin $1_A$ receptor, yet lack mutagenic potential as measured by assays of chromosomal aberration. The compounds are particularly useful for alleviating the symptoms of nicotine and tobacco withdrawal, and for the treatment of depression and other conditions for which serotonin reuptake inhibitors are used.

5 Claims, No Drawings

COMPOUNDS HAVING EFFECTS ON SEROTONIN-RELATED SYSTEMS

This application claims priority to provisional application No. 60/020,131 filed Jun. 20, 1996.

FIELD OF THE INVENTION

The present invention belongs to the fields of pharmacology and medicinal chemistry, and provides new pharmaceuticals which are useful for the treatment of diseases which are caused or affected by disorders of the serotonin-affected neurological systems, particularly those relating to the serotonin $1_A$ receptor and those relating to the reuptake of serotonin.

BACKGROUND OF THE INVENTION

Pharmaceutical researchers have discovered in recent years that the neurons of the brain which contain monoamines are of extreme importance in a great many physiological processes which very strongly affect many psychological and personality-affecting processes as well. In particular, serotonin (5-hydroxytryptamine; 5-HT) has been found to be a key to a very large number of processes which affect both physiological and psychological functions. Drugs which influence the function of serotonin in the brain are accordingly of great importance and are now used for a surprisingly large number of different therapies.

The early generations of serotonin-affecting drugs tended to have a variety of different physiological functions, considered from both the mechanistic and therapeutic points of view. For example, many of the tricyclic antidepressant drugs are now known to be active as inhibitors of serotonin reuptake, and also to have anticholinergic, antihistaminic or anti-α-adrenergic activity. More recently, it has become possible to study the function of drugs at individual receptors in vitro or ex vivo, and it has also been realized that therapeutic agents free of extraneous mechanisms of action are advantageous to the patient. Accordingly, the objective of research now is to discover agents which affect only functions of serotonin, for example, at a single identifiable receptor.

The present invention provides compounds which have highly selective activity as antagonists and partial agonists of the serotonin $1_A$ receptor and a second activity as inhibitors of reuptake of serotonin. The best-known pharmaceutical with the latter efficacy is fluoxetine, and the importance of its use in the treatment of depression and other conditions is extremely well documented and publicized. Recent scientific articles, for example, Artigas, TIPS, 14, 262 (1993), have suggested that the efficacy of a reuptake inhibitor may be decreased by the activation of serotonin $1_A$ receptors with the resultant reduction in the firing rate of serotonin neurons. Accordingly, present research in the central nervous system is focusing on the effect of combining reuptake inhibitors with compounds which affect the 5HT-$1_A$ receptor.

Compounds exhibiting both serotonin reuptake inhibition activity and 5-HT$_{1A}$ antagonist activity have been described (U.S. Ser. Nos. 08/373,823 and 08/468,900). Surprisingly, it has been found that the compounds of the present invention are potent serotonin reuptake inhibitors and antagonists of the 5HT-$1_A$ receptor, yet lack the mutagenic potential of structurally similar compounds as measured in chromosomal aberration assays.

SUMMARY OF THE INVENTION

The present invention provides a series of new compounds, methods of using them for pharmaceutical purposes, and pharmaceutical compositions whereby the compounds may be conveniently administered. The invention provides the following compounds of formula I:

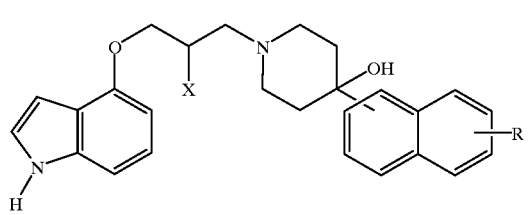

where
X is hydrogen or hydroxy;
R is hydrogen, hydroxy, cyano, $C_1$–$C_6$ alkyl, $C_1$–$C_6$ acyl, $C_2$–$C_6$ alkenyl, $C_2$–$C_6$ alkynyl, aryl, $C_1$–$C_6$ alkoxy, aryloxy, aryl-($C_1$–$C_4$ alkylene)oxy, $C_1$–$C_6$ alkyl—S(O)$_n$—, aryl—S(O)$_n$—, —NR$^1$R$^2$, or —C(O)NR$^1$R$^2$;
n is 0, 1 or 2; and
R$^1$ and R$^2$ are independently hydrogen, $C_1$–$C_6$ alkyl, or phenyl, or taken together with the nitrogen to which they are attached form a ring of formula:

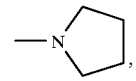

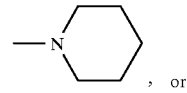
, or

where R$^3$ is hydrogen, $C_1$–$C_6$ alkyl, phenyl, benzyl, or —C(O)O—($C_1$–$C_6$ alkyl); and pharmaceutically acceptable salts thereof.

Further, pharmaceutical methods of use combining activity at the $1_A$ receptor and inhibition of serotonin reuptake are carried out by the administration of compounds of formula I.

More specific methods of treatment include a method of alleviating the symptoms caused by withdrawal or partial withdrawal from the use of tobacco or of nicotine; a method of treating anxiety; and a method of treating a condition chosen from the group consisting of depression, hypertension, cognitive disorders, psychosis, sleep disorders, gastric motility disorders, sexual dysfunction, brain trauma, memory loss, eating disorders and obesity, substance abuse, obsessive-compulsive disease, panic disorder and migraine; which methods comprise administering to a subject in need of such treatment an effective amount of a compound of Formula I.

Further, the administration of a compound of Formula I also provides a method of treating a condition chosen from the group consisting of obsessive-compulsive disease, obesity, migraine, pain, particularly neuropathic pain, bulimia, premenstrual syndrome or late luteal syndrome, alcoholism, tobacco abuse, anxiety, post-traumatic stress disorder, memory loss, dementia of aging, social phobia, attention-deficit hyperactivity disorder, disruptive behavior disorders, impulsive control disorders, borderline personality disorder, chronic fatigue syndrome, premature ejaculation, erectile difficulty, anorexia nervosa, disorders of sleep, autism, mutism and trichotilomania.

DESCRIPTION OF PREFERRED EMBODIMENTS

In the present document, all descriptions of concentrations, amounts, ratios and the like will be expressed in weight units unless otherwise stated. All temperatures are in degrees Celsius.

The Compounds

In the general description, the general chemical terms are all used in their normal and customary meanings. "$C_1$–$C_6$ alkyl" means methyl, ethyl, propyl, isopropyl, butyl, isobutyl, sec-butyl, tert-butyl, and the like. "$C_1$–$C_6$ acyl" means formyl, acetyl, propanoyl, butanoyl, 2-methylbutanoyl, and the like. "$C_2$-$C_6$ alkenyl", means ethylenyl, propen-1-yl, propen-2-yl, propen-3-yl, and the like. "$C_2$-$C_6$ alkynyl" means ethynyl, propynyl, 1-propyn-3-yl, and the like. "$C_1$–$C_6$ alkoxy" means methoxy, propoxy, isopropoxy, and the like.

"Aryl" means a phenyl moiety or a heterocyclic moiety selected from the group consisting of pyridinyl, furyl, thienyl, pyrrolyl, pyrazolyl, isoxazolyl, thiazolyl, oxazolyl, imidazolyl, and triazolyl.

"Aryloxy" is taken to mean an aryl group bonded to an oxygen atom. Such groups include phenoxy, pyridinyloxy, thienyloxy, and the like.

"Aryl-($C_1$–$C_4$ alkylene)oxy" is taken to mean an aryl moiety tethered to an oxygen atom by a methylene chain of from 1 to 4 carbons. Such groups include benzyloxy, phenethyloxy, pyridinylpropyloxy, and the like.

The compounds described in this document are highly active, important and particularly useful in the treatment methods of the present invention, but certain classes of the compounds are preferred. The following paragraphs describe such preferred classes:

a) the naphthyl moiety is bonded to the rest of the molecule via the 2-position;
b) X is hydroxy;
c) R is hydrogen;
d) R is hydroxy;
e) R is $C_1$–$C_6$ alkoxy;
f) R is methoxy;
g) R is other than hydrogen and is attached to the 6-position of the naphthyl moiety;
h) R is methoxy attached to the 7-position of the naphthyl moiety;
i) the compound is in the (S)-(−) form;
j) R is hydrogen, hydroxy, $C_1$–$C_6$ alkoxy or aryl-($C_1$–$C_4$ alkylene)oxy;
k) R is aryloxy, hydrogen or hydroxy;
l) R is cyano, $C_1$–$C_6$ alkyl, $C_2$–$C_6$ alkenyl or $C_2$–$C_6$ alkynyl;
m) R is $C_1$–$C_6$ acyl, aryl, —NR$^1$R$^2$ or —C(O)NR$^1$R$^2$;
n) R is $C_1$–$C_6$ alkyl—S(O)$_n$—, or aryl —S(O)$_n$—;
o) R is aryl-($C_1$–$C_4$ alkylene)oxy;
p) R is hydrogen, hydroxy, $C_1$–$C_6$ alkyl, aryl, $C_1$–$C_6$ alkoxy, aryloxy or aryl-($C_1$–$C_4$ alkylene)oxy.

The reader will understand that the above preferred classes of compounds may be combined to form additional, broader or narrower classes of preferred compounds.

Since the compounds of this invention are basic in nature, they accordingly react with any of a number of inorganic and organic acids to form pharmaceutically acceptable acid addition salts. Since some of the free amines of the compounds of this invention are typically oils at room temperature, it is preferable to convert the free amines to their pharmaceutically acceptable acid addition salts for ease of handling and administration, since the latter are routinely solid at room temperature. Acids commonly employed to form such salts are inorganic acids such as hydrochloric acid, hydrobromic acid, hydroiodic acid, sulfuric acid, phosphoric acid, and the like, and organic acids, such as p-toluenesulfonic acid, methanesulfonic acid, oxalic acid, p-bromophenylsulfonic acid, carbonic acid, succinic acid, citric acid, benzoic acid, acetic acid and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, β-hydroxybutyrate, glycollate, tartrate, methanesulfonate, propanesulfonate, naphthalene-1-sulfonate, naphthalene-2-sulfonate, mandelate and the like. Preferred pharmaceutically acceptable salts are those formed with hydrochloric acid, oxalic acid or maleic acid.

Many of the compounds of Formula I can form optical isomers. In particular, the compounds wherein X is hydroxy have an asymmetric center at the carbon atom to which X is attached. In general, it is preferred for the asymmetric center to which X is attached to exist in the S-(−) form. However, when a compound of the present invention is named without an indication of asymmetric form, any and all of the possible asymmetric forms are intended.

Synthesis

The synthesis of the present compounds is carried out by methods which are conventional for the synthesis of related known compounds. The syntheses, in general, comprise the reaction of an intermediate which supplies the indole-4-oxypropane group with an intermediate piperidine which supplies the amine group of formula:

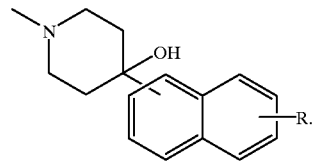

V

When a compound where X is hydroxy is to be prepared, the most useful intermediate is 4-oxiranylalkoxyindole, which is readily reacted with an appropriate piperidine which provides the group of formula V. The oxiranyl intermediate is readily prepared by known methods as the racemate or either enantiomer. The oxiranyl group readily reacts with the nitrogen of the appropriate piperidine to prepare the desired product in good yield. Moderate reaction conditions, such as from ambient temperature to about 100°, are satisfactory, and any solvent which is inert to the reactants and has adequate solvency for them may be used.

It has been found that a preferred reaction condition is the reflux temperature at ambient pressure in an alcohol such as methanol. No catalyst or activating agent is necessary, and conventional isolation procedures are effective. The examples below illustrate the synthesis of many compounds of the present invention by such processes. When the process is carried out with intermediates in a single asymmetric form, little or no racemization has been observed, so that the products are obtained in the desired single asymmetric form.

Another convenient method of synthesis of the present compounds is by use of a 1-chloro-3-(indol-4-yloxy) propane. Alternatively, other leaving groups besides chloro may be used on the 3-(indol-4-oxy)propane, of course, such as sulfonates, particularly methanesulfonate or toluenesulfonate, bromo, and the like. The 3-(indol-4-yloxy) propane intermediate is reacted with the appropriate amine in the presence of any convenient acid scavenger. The usual bases such as alkali metal or alkaline earth metal carbonates, bicarbonates and hydroxides are useful acid scavengers, as are some organic bases such as trialkylamines and trialkanolamines. The reaction medium for such reactions may be any convenient organic solvent which is inert to the basic conditions; acetonitrile, esters such as ethyl acetate and the like and halogenated alkane solvents are useful, as organic chemists will readily understand. Usually the reactions will be carried out at elevated temperatures such as from ambient temperature to the reflux temperature of the reaction mixture, particularly from about 50° to about 100°.

Methods of synthesis of indole intermediates are found in the literature, together with methods of preparing the isolated enantiomers thereof, and the reader will require no assistance to obtain them.

Similarly, the requisite piperidines are all prepared by conventional procedures which may be found in the literature.

Thus, the general process for preparing the present compounds has two main variations, which may briefly be described as follows:

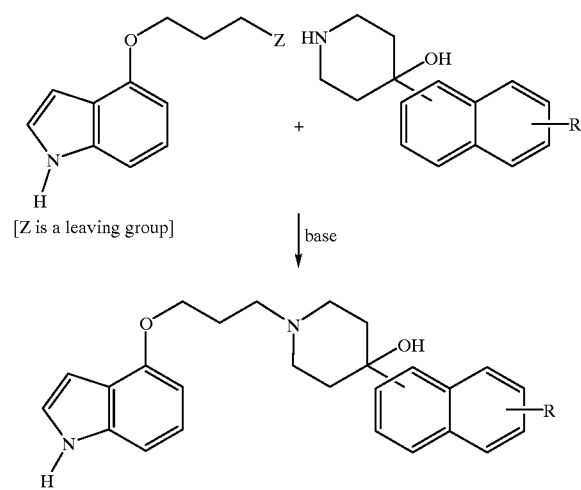

In the following Examples and Preparations, the abbreviation MS(FD) means field desorption mass spectroscopy.

PREPARATION I 1-benzyl-4-hydroxy-4-(naphth-1-yl)piperidine

A solution of 48.7 mL (63.3 mMol) sec-butyllithium (1.3 M in tetrahydrofuran) was added to a solution of 10.0 gm (42.2 mMol) 1-bromonaphthalene in 200 mL tetrahydrofuran at −78° C. The reaction mixture was stirred at that temperature for 1.5 hours and to it was then added a solution of 8.2 mL (44.3 mMol) 1-benzyl-4-piperidone in 40 mL tetrahydrofuran dropwise. The reaction mixture was allowed to warm to room temperature and was then quenched by the addition of 2N sodium hydroxide. The resulting mixture was extracted well with diethyl ether. The combined organic extracts were washed with saturated aqueous sodium chloride, dried over sodium sulfate and concentrated under reduced pressure. The residue was subjected to flash silica gel chromatography, eluting with dichloromethane which contained 0–2% methanol. Fractions containing product were combined and concentrated under reduced pressure to provide 4.34 gm (32%) of the desired compound as a white foam.

PREPARATION II 1-benzyl-4-hydroxy-4-(naphth-2-yl)piperidine

Beginning with 6.0 gm (29.0 mMol) 2-bromonaphthalene, 4.84 gm (53%) of the title compound were recovered as a white solid by the procedure described in Preparation I.

PREPARATION III 1-benzyl-4-hydroxy-4-(6-methoxynaphth-2-yl) piperidine

Beginning with 5.0 gm (21.10 mMol) 2-bromo-6-methoxynaphthalene, 4.62 gm (63%) of the title compound were recovered as a white solid by the procedure described in Preparation I.

PREPARATION IV 4-hydroxy-4-(7-methoxynaphth-2-yl)piperidine

Beginning with 5.0 gm (21.10 mMol) of 2-bromo-7-methoxynaphthlene, 5.21 gm (71%) of the title compound were recovered as a white solid by the procedure described in Preparation I.

General Procedure for the Preparation of Alkoxynaphthalenes

A solution of an appropriate hydroxynaphthalene in dimethylformamide is added dropwise to a stirred suspension of 1.05 equivalents sodium hydride in dimethylformamide at 0° C. The reaction mixture is stirred at this temperature for about 1.5 hours and then a solution of 1.2 equivalents of an appropriate alkylating agent, for example, an alkyl or arylalkylene halide, mesylate, tosylate or triflate, in dimethylformamide is added and the reaction mixture allowed to warm to room temperature. After stirring for about 18 hours at room temperature the reaction mixture is partitioned between ethyl acetate and saturated aqueous sodium bicarbonate. The organic phase is washed with saturated aqueous sodium chloride, dried over sodium sulfate and concentrated under reduced pressure. The residue is purified by flash silica chromatography, crystallization or distillation if necessary, or may used directly in subsequent steps.

PREPARATION V 1-benzyl-4-hydroxy-4-(6-ethoxynaphth-2-yl)piperidine

Beginning with 5.0 gm (19.9 mMol) 2-bromo-6-ethoxynaphthalene, 4.65 gm (65%) of the title compound were recovered as a white solid by the procedure described in Preparation I.

PREPARATION VI 1-benzyl-4-hydroxy-4-(6-propoxynaphth-2-yl)piperidine

Beginning with 7.0 gm (26.4 mMol) 2-bromo-6-propoxynaphthalene, 5.38 gm (54%) of the title compound were recovered as an off-white solid by the procedure described in Preparation I.

PREPARATION VII 1-benzyl-4-hydroxy-4-(6-isopropoxynaphth-2-yl)piperidine

Beginning with 5.0 gm (18.9 mMol) 2-bromo-6-isopropoxynaphthalene, 3.89 gm (55%) of the title compound were recovered as a viscous yellow oil by the procedure described in Preparation I.

PREPARATION VIII 1-benzyl-4-hydroxy-4-(6-hexyloxynaphth-2-yl)piperidine

Beginning with 10.0 gm (19.9 mMol) 2-bromo-6-hexyloxynaphthalene, 8.89 gm (65%) of the title compound were recovered as a white solid by the procedure described in Preparation I.

PREPARATION IX 1-benzyl-4-hydroxy-4-(6-phenethyloxynaphth-2-yl)piperidine

Beginning with 4.0 gm (12.2 mMol) 2-bromo-6-phenethyloxynaphthalene, 2.77 gm (52%) of the title compound were recovered as colorless oil by the procedure described in Preparation I.

PREPARATION X 1-tert-butyloxycarbonyl-4-hydroxy-4-(6-benzyloxynaphth-2-yl)piperidine Beginning with 5.0 gm (15.9 mMol) 2-bromo-6-benzyloxynaphthalene and 3.34 gm (16.8 mMol) 1-tert-butyloxycarbonyl-4-piperidone, 2.31 gm (33%) of the title compound were recovered as a white solid by the procedure described in Preparation I.

PREPARATION XI 1-benzyl-4-hydroxy-4-(6-hydroxynaphth-2-yl)piperidine

A solution of 10.0 gm (44.8 mMol) 2-bromo-6-hydroxynaphthalene in tetrahydrofuran was added dropwise to a suspension of 9.42 gm (47.1 mMol) potassium hydride (20% suspension) in 180 mL tetrahydrofuran at 0° C. After stirring at this temperature for 2 hours the reaction mixture was cooled further to −78° C. and to it was added dropwise 58 mL (98.6 mMol) tert-butyllithium (1.7M in tetrahydrofuran). The mixture was stirred for 20 minutes at this temperature and then a solution of 8.73 mL (47.1 mMol) 1-benzyl-4-piperidone in 30 mL tetrahydrofuran was added dropwise. The reaction mixture was allowed to warm gradually to room temperature and was stirred at this temperature for 18 hours. The reaction mixture was then partitioned between ethyl acetate and dilute ammonium hydroxide. The phases were separated and the aqueous phase was extracted well with ethyl acetate. The organic phases were combined, washed with saturated aqueous sodium chloride, dried over sodium sulfate and concentrated under reduced pressure. The residue was subjected to flash silica gel chromatography, eluting with 5% methanol in dichloromethane. Fractions containing product were combined and concentrated under reduced pressure to provide 2.27 gm (15%) of the desired product.

MS(FD): m/e=333 (M$^+$); EA: Calculated for $C_{22}H_{23}NO_2$: C, 79.25; H, 6.95; N, 4.20. Found: C, 79.00; H, 6.88; N, 3.97.

PREPARATION XII 4-hydroxy-4-(naphth-1-yl)piperidine

A mixture of 1.5 gm (4.7 mMol) 1-benzyl-4-hydroxy-4-(naphth-1-yl)piperidine and 0.1 gm 5% palladium on carbon in 45 mL methanol was stirred under a hydrogen atmosphere for 2 days at room temperature. The reaction mixture was then filtered through a bed of celite and the filtrate concentrated under reduced pressure. The residue was subjected to flash silica gel chromatography, eluting with dichloromethane containing 17% methanol. Fractions containing product were combined and concentrated under reduced pressure to provide 0.526 gm (49%) of the title compound as a white solid.

EA: Calculated for $C_{15}H_{17}NO$: C, 79.26; H, 7.54; N, 6.16. Found: C, 79.18; H, 7.79; N, 6.38.

The following Preparations XIII through XXIII were carried out by the above process.

PREPARATION XIII 4-hydroxy-4-(naphth-2-yl)piperidine

Beginning with 0.600 gm (1.8 mMol) 1-benzyl-4-hydroxy-4-(naphth-2-yl)piperidine, 0.262 gm (61%) of the title compound were recovered as a white foam. The compound was converted to the oxalate hemihydrate for characterization.

EA: Calculated for $C_{15}H_{17}NO \cdot C_2H_2O_4 \cdot 0.5\ H_2O$: C, 62.56; H, 6.14; N, 4.29. Found: C, 62.72; H, 6.21; N, 4.03.

PREPARATION XIV 4-hydroxy-4-(6-methoxynaphth-2-yl)piperidine

Beginning with 1.00 gm (2.9 mMol) 1-benzyl-4-hydroxy-4-(6-methoxynaphth-2-yl)piperidine, 0.637 gm (86%) of the title compound were recovered as a white foam. The compound was converted to the oxalate salt for characterization.

MS(FD): m/e=257 ($M^+$); EA: Calculated for $C_{15}H_{17}NO \cdot C_2H_2O_4$: C, 62.24; H, 6.09; N, 4.03. Found: C, 62.17; H, 6.05; N, 3.87.

PREPARATION XV 4-hydroxy-4-(6-ethoxynaphth-2-yl)piperidine

Beginning with 1.0 gm (2.8 mMol) 1-benzyl-4-hydroxy-4-(6-ethoxynaphth-2-yl)piperidine, 0.498 gm (67%) of the title compound were recovered.

MS(FD): m/e=271 ($M^+$); EA: Calculated for $C_{15}H_{17}NO$: C, 75.25; H, 7.80; N, 5.16. Found: C, 75.45; H, 7.52; N, 5.05.

PREPARATION XVI 4-hydroxy-4-(6-propoxynaphth-2-yl)piperidine

Beginning with 2.0 gm (5.3 mMol) 1-benzyl-4-hydroxy-4-(6-propoxynaphth-2-yl)piperidine, 1.31 gm (86%) of the title compound were recovered as an off-white foam.

MS(FD): m/e=285 ($M^+$)

PREPARATION XVII 4-hydroxy-4-(6-propoxynaphth-2-yl)piperidine

Beginning with 2.0 gm (5.3 mMol) 1-benzyl-4-hydroxy-4-(6-propoxynaphth-2-yl)piperidine, 1.31 gm (86%) of the title compound were recovered as an off-white foam.

MS(FD): m/e=285 ($M^+$)

PREPARATION XVIII 4-hydroxy-4-(6-isopropoxynaphth-2-yl)piperidine

Beginning with 2.0 gm (5.3 mMol) 1-benzyl-4-hydroxy-4-(6-isopropoxynaphth-2-yl)piperidine, 0.33 gm (30%) of the title compound were recovered as a white solid.

PREPARATION XIX 4-hydroxy-4-(6-hexyloxynaphth-2-yl)piperidine

Beginning with 3.0 gm (7.2 mMol) 1-benzyl-4-hydroxy-4-(6-hexyloxynaphth-2-yl)piperidine, 2.3 gm (98%) of the title compound were recovered as an off-white solid.

MS(FD): m/e=328 (M+1)

PREPARATION XX 4-hydroxy-4-(6-phenethyloxynaphth-2-yl)piperidine

Beginning with 2.77 gm (6.3 mMol) 1-benzyl-4-hydroxy-4-(6-phenethyloxynaphth-2-yl)piperidine, 0.42 gm (19%) of the title compound were recovered as a white solid.

PREPARATION XXI 4-hydroxy-4-(6-hydroxynaphth-2-yl)piperidine

Beginning with 0.900 gm (2.7 mMol) 1-benzyl-4-hydroxy-4-(6-hydroxynaphth-2-yl)piperidine, 0.506 gm (77%) of the title compound were recovered as a tan solid.

MS(FD): m/e=243 ($M^+$)

PREPARATION XXII 4-hydroxy-4-(6-benzyloxynaphth-2-yl)piperidine

A solution of 4.5 gm (10.4 mMol) 1-tert-butoxycarbonyl-4-hydroxy-4-(6-benzyloxynaphth-2-yl)piperidine, 5 mL 5N hydrochloric acid in 20 mL ethyl acetate and 20 mL tetrahydrofuran was stirred at room temperature for 18 hours. The reaction mixture was then partitioned between ethyl acetate and 2N sodium hydroxide. The phases were separated and the aqueous phase extracted well with ethyl acetate. The combined extracts were washed with saturated aqueous sodium chloride, dried over sodium sulfate and concentrated under reduced pressure. The residue was subjected to flash silica gel chromatography, eluting with 10% methanol in dichloromethane. Fractions containing product were combined and concentrated under reduced pressure to provide 0.814 gm (24%) of the title compound.

MS(FD): m/e=271 ($M^+$); EA: Calculated for $C_{22}H_{23}NO_2$: C, 79.25; H, 6.95; N, 4.20. Found: C, 78.97; H, 7.17; N, 4.14.

PREPARATION XXIII (S)-(+)-4-(oxiranylmethoxy)-1H-indole.

A 3.2 g portion of 4-hydroxy-1H-indole was dissolved in 31 mL of dimethylformamide in a 50 mL flask equipped with a magnetic stirrer, nitrogen bubbler and thermometer. To it was added 1.27 g of sodium methoxide and the mixture was stirred until a blue-black solution resulted. The warm mixture was placed under vacuum for 5 minutes to remove most of the resulting methanol. To the mixture was added 6 g of oxiranylmethoxysulfonyl-3-nitrobenzene, resulting in an exotherm to about 37° C. The mixture was stirred at ambient temperature for 1 hour, and was then poured into a separatory funnel containing 55 mL of methyl t-butyl ether and 80 mL of water. The mixture was shaken well, and the layers were separated. The organic layer was removed and the aqueous layer was extracted with 2×55 mL of methyl t-butyl ether. The organic layers were combined and back-extracted with 50 mL of 5% aqueous lithium chloride. The layers were separated again, and the organic layer was dried with magnesium sulfate and filtered. The organic filtrate was concentrated under vacuum to about 15 mL of volume, and was seeded with pure desired product and stirred. The product was crystallized to a thick slurry to which 20 mL of heptane was slowly added. The mixture was stirred for one hour more and filtered, and the filter cake was rinsed with 3:1 heptane:methyl t-butyl ether, and then with heptane. The product was dried in a vacuum oven at 40° C. to obtain about 3.5 g of product.

EXAMPLE 1

1-(4-indolyloxy)-3-[4-hydroxy-4-(6-hydroxynaphth-2-yl)piperidine-1-yl]propane oxalate A mixture of 0.172 gm (0.82 mMol) 1-(4-indolyloxy)-3-chloropropane, 0.200 gm (0.82 mMol) 4-hydroxy-4-(6- hydroxynaphth-2-yl)piperidine, and 0.17 gm (1.2 mMol) potassium carbonate in 6 mL acetonitrile were stirred at reflux for 18 hours. The reaction mixture was cooled to room temperature and then partitioned between ethyl acetate and 2N sodium hydroxide. The phases were separated and the aqueous phase extracted well with ethyl acetate. The combined organic phases were washed with saturated aqueous sodium chloride, dried over sodium sulfate and concentrated under reduced pressure. The resulting residue was subjected to radial chromatography (silica, 2 mm plate), eluting with 2% methanol in dichloromethane containing a trace of ammonium hydroxide. Fractions shown to contain product were combined and concentrated under reduced pressure to provide 0.085 gm (25%) 1-(4-indolyloxy)-3-[4-hydroxy-4-(6-hydroxynaphth-2-yl)piperidine-1-yl]propane as a foam. The oxalate salt was prepared to provide the title compound.

MS(FD): m/e=416 (M$^+$); EA: Calculated for $C_{26}H_{28}N_2O_3 \cdot C_2H_2O_4$: C, 66.39; H, 5.97; N, 5.53. Found: C, 66.47; H, 6.07; N, 5.45.

EXAMPLE 2

1-(4-indolyloxy)-3-[4-hydroxy-4-(6-methoxynaphth-2-yl)piperidine-1-yl]propane oxalate Beginning with 0.204 gm (0.97 mMol) 1-(4-indolyloxy)-3-chloropropane and 0.250 gm (0.97 mMol) 4-hydroxy-4-(6-methoxynaphth-2-yl)piperidine, 0.210 gm (50%) of 1-(4-indolyloxy)-3-[4-hydroxy-4-(6-methoxynaphth-2-yl) piperidine-1-yl]propane was recovered by the procedure described in Example 1. The oxalate salt was prepared to provide the title compound.

MS(FD): m/e=431 (M$^+$); EA: Calculated for $C_{27}H_{30}N_2O_3 \cdot C_2H_2O_4$: C, 66.91; H, 6.20; N, 5.38. Found: C, 67.62; H, 6.67; N, 5.46.

EXAMPLE 3

1-(4-indolyloxy)-3-[4-hydroxy-4-(6-ethoxynaphth-2-yl)piperidine-1-yl]propane

Beginning with 0.155 gm (0.70 mMol) 1-(4-indolyloxy)-3-chloropropane and 0.155 gm (0.70 mMol) 4-hydroxy-4-(6-ethoxynaphth-2-yl)piperidine, 0.140 gm (43%) of the title compound was recovered as a white solid by the procedure described in Example 1.

MS(FD): m/e=444 (M$^+$); EA: Calculated for $C_{28}H_{32}N_2O_3$: C, 75.64; H, 7.26; N, 6.30. Found: C, 75.45; H, 7.02; N, 6.27.

EXAMPLE 4

1-(4-indolyloxy)-3-[4-hydroxy-4-(6-propoxynaphth-2-yl)piperidine-1-yl]propane oxalate Beginning with 0.220 gm (1.1 mMol) 1-(4-indolyloxy)-3-chloropropane and 0.300 gm (1.1 mMol) 4-hydroxy-4-(6-propoxynaphth-2-yl)piperidine, 0.190 gm (39%) of 1-(4-indolyloxy)-3-[4-hydroxy-4-(6-methoxynaphth-2-yl) piperidine-1-yl]propane was recovered as an off-white solid by the procedure described in Example 1. The oxalate salt was prepared to provide the title compound.

MS(FD): m/e=459 (M$^+$); EA: Calculated for $C_{29}H_{34}N_2O_3 \cdot C_2H_2O_4$: C, 67.86; H, 6.61; N, 5.11. Found: C, 68.09; H, 6.64; N, 5.21.

EXAMPLE 5

1-(4-indolyloxy)-3-[4-hydroxy-4-(6-isopropoxynaphth-2-yl)piperidine-1-yl]propane oxalate Beginning with 0.110 gm (0.50 mmol) 1-(4-indolyloxy)-3-chloropropane and 0.150 gm (0.50 mMol) 4-hydroxy-4-(6-isopropoxynaphth-2-yl)piperidine, 0.135 gm (56%) of 1-(4-indolyloxy)-3-[4-hydroxy-4-(6-isopropoxynaphth-2-yl)piperidine-1-yl]propane was recovered as a white solid by the procedure described in Example 1. The oxalate salt was prepared to provide the title compound.

MS(FD): m/e=458 (M$^+$); EA: Calculated for $C_{29}H_{34}N_2O_3 \cdot C_2H_2O_4$: C, 67.87; H, 6.61; N, 5.11. Found: C, 68.10; H, 6.66; N, 5.01.

EXAMPLE 6

1-(4-indolyloxy)-3-[4-hydroxy-4-(6-hexyloxynaphth-2-yl)piperidine-1-yl]propane

Beginning with 0.257 gm (1.2 mMol) 1-(4-indolyloxy)-3-chloropropane and 0.400 gm (1.2 mMol) 4-hydroxy-4-(6-hexyloxynaphth-2-yl)piperidine, 0.194 gm (32%) of the title compound was recovered as a white solid by the procedure described in Example 1.

MS(FD): m/e=500 (M$^+$); EA: Calculated for $C_{32}H_{40}N_2O_3$: C, 76.77; H, 8.05; N, 5.59. Found: C, 76.84; H, 8.20; N, 5.44.

EXAMPLE 7

1-(4-indolyloxy)-3-[4-hydroxy-4-(6-benzyloxynaphth-2-yl)piperidine-1-yl]propane

Beginning with 0.189 gm (0.90 mMol) 1-(4-indolyloxy)-3-chloropropane and 0.300 gm (0.90 mMol) 4-hydroxy-4-(6-benzyloxynaphth-2-yl)piperidine, 0.137 gm (30%) of the title compound was recovered as a white solid by the procedure described in Example 1.

MS(FD): m/e=506 (M$^+$); EA: Calculated for $C_{33}H_{34}N_2O_3$: C, 78.23; H, 6.76; N, 5.53. Found: C, 78.40; H, 6.73; N, 5.64.

EXAMPLE 8

1-(4-indolyloxy)-3-[4-hydroxy-4-(6-phenethyloxynaphth-2-yl)piperidine-1-yl]propane oxalate Beginning with 0.121 gm (0.60 mMol) 1-(4-indolyloxy)-3-chloropropane and 0.200 gm (0.60 mMol) 4-hydroxy-4-(6-phenethyloxynaphth-2-yl)piperidine, 0.163 gm (54%) of 1-(4-indolyloxy)-3-[4-hydroxy-4-(6-phenethyloxynaphth-2-yl)piperidine-1-yl]propane was recovered as a white solid by the procedure described in Example 1. The oxalate salt was prepared to provide the title compound.

MS(FD): m/e=520 (M$^+$); EA: Calculated for $C_{34}H_{36}N_2O_3 \cdot C_2H_2O_4$: C, 70.80; H, 6.27; N, 4.59. Found: C, 70.87; H, 6.36; N, 4.86.

EXAMPLE 9

(2S)-(−)-1-(4-indolyloxy)-3-[4-hydroxy-4-(naphth-1-yl)piperidine-1-yl]-2-propanol A mixture of 0.167 gm (0.88 mMol) (S)-(+)-4-(oxiranylmethoxy)-1H-indole and 0.200 gm (0.88 mmol) 4-hydroxy-4-(naphth-1-yl)piperidine in 10 mL methanol was heated to reflux for 18 hours. The reaction mixture was cooled to room temperature and was then partitioned between ethyl acetate and 2N sodium hydroxide. The phases were separated and the aqueous phase extracted again with ethyl acetate. The organic phases were combined, washed with saturated aqueous sodium chloride and concentrated under reduced pressure. The residue was subjected to flash silica gel chromatography, eluting with 5% methanol in dichloromethane. Fractions containing product were combined and concentrated under reduced pressure to provide 0.309 (84%) of the title compound as an off-white solid.

MS(FD): m/e=417 (M$^+$) EA: Calculated for $C_{26}H_{28}N_2O_3$: C, 74.98; H, 6.78; N, 6.73. Found: C, 74.62; H, 6.91; N, 7.90.

EXAMPLE 10

(2S)-(−)-1-(4-indolyloxy)-3-[4-hydroxy-4-(naphth-2-yl)piperidine-1-yl]-2-propanol oxalate Beginning with 0.129 gm (0.70 mMol) (S)-(+)-4-(oxiranylmethoxy)-1H-indole and 0.175 gm (0.70 mMol) 4-hydroxy-4-(naphth-2-yl)piperidine, 0.199 gm (70%) (2S)-(−)-1-(4-indolyloxy)-3-[4-hydroxy-4-(naphth-2-yl)piperidine-1-yl]-2-propanol were recovered as a white foam by the procedure described in Example 9. The oxalate salt was prepared to provide the title compound.

MS(FD): m/e=417 (M$^+$);

EXAMPLE 11

(2S)-(−)-1-(4-indolyloxy)-3-[4-hydroxy-4-(6-hydroxynaphth-2-yl)piperidine-1-yl]-2-propanol oxalate Beginning with 0.156 gm (0.82 mMol) (S)-(+)-4-(oxiranylmethoxy)-1H-indole and 0.200 gm (0.82 mmol) 4-hydroxy-4-(6-hydroxynaphth-2-yl)piperidine, 0.104 gm (29%) (2S)-(−)-1-(4-indolyloxy)-3-[4-hydroxy-4-(6-hydroxynaphth-2-yl)piperidine-1-yl]-2-propanol were recovered as a white foam by the procedure described in Example 9. The oxalate salt was prepared to provide the title compound.

MS(FD): m/e=432 (M$^+$)

EXAMPLE 12

(2S)-(−)-1-(4-indolyloxy)-3-[4-hydroxy-4-(6-methoxynaphth-2-yl)piperidine-1-yl]-2-propanol oxalate Beginning with 0.184 gm (0.97 mMol) (S)-(+)-4-(oxiranylmethoxy)-1H-indole and 0.250 gm (0.97 mMol) 4-hydroxy-4-(6-methoxynaphth-2-yl)piperidine, 0.212 gm (49%) (2S)-(−)-1-(4-indolyloxy)-3-[4-hydroxy-4-(6-methoxynaphth-2-yl)piperidine-1-yl]-2-propanol were recovered by the procedure described in Example 9. The oxalate salt was prepared to provide the title compound.

MS(FD) m/e=447 (M$^+$)

EXAMPLE 13

(2S)-(−)-1-(4-indolyloxy)-3-[4-hydroxy-4-(6-ethoxynaphth-2-yl)piperidine-1-yl]-2-propanol Beginning with 0.139 gm (0.70 mMol) (S)-(+)-4-(oxiranylmethoxy)-1H-indole and 0.200 gm (0.70 mMol) 4-hydroxy-4-(6-ethoxynaphth-2-yl)piperidine, 0.191 gm (56%) of the title compound were recovered as a white solid by the procedure described in Example 9.

MS(FD): m/e=460 (M$^+$); EA: Calculated for $C_{28}H_{32}N_2O_4$: C, 73.02; H, 7.00; N, 6.08. Found: C, 73.11; H, 6.83; N, 6.16.

EXAMPLE 14

(2S)-(−)-1-(4-indolyloxy)-3-[4-hydroxy-4-(6-propoxynaphth-2-yl)piperidine-1-yl]-2-propanol Beginning with 0.199 gm (1.1 mMol) (S)-(+)-4-(oxiranylmethoxy)-1H-indole and 0.300 gm (1.1 mMol) 4-hydroxy-4-(6-propoxynaphth-2-yl)piperidine, 0.289 gm (60%) of the title compound were recovered as an off-white solid by the procedure described in Example 9.

MS(FD): m/e=475 (M+1) EA: Calculated for $C_{29}H_{34}N_2O_4$: C, 73.39; H, 7.22; N, 5.90. Found: C, 73.27; H, 7.16; N, 5.84.

EXAMPLE 15

(2S)-(−)-1-(4-indolyloxy)-3-[4-hydroxy-4-(6-isopropoxynaphth-2-yl)piperidine-1-yl]-2-propanol Beginning with 0.099 gm (0.50 mMol) (S)-(+)-4-(oxiranylmethoxy)-1H-indole and 0.150 gm (0.50 mMol) 4-hydroxy-4-(6-isopropoxynaphth-2-yl)piperidine, 0.165 gm (66%) of the title compound were recovered as a white solid by the procedure described in Example 9.

MS(FD): m/e=474 (M$^+$) EA: Calculated for $C_{29}H_{34}N_2O_4$: C, 73.39; H, 7.22; N, 5.90. Found: C, 73.55; H, 7.08; N, 5.74.

EXAMPLE 16

(2S)-(−)-1-(4-indolyloxy)-3-[4-hydroxy-4-(6-hexyloxynaphth-2-yl)piperidine-1-yl]-2-propanol Beginning with 0.232 gm (1.2 mMol) (S)-(+)-4-(oxiranylmethoxy)-1H-indole and 0.400 gm (1.2 mMol) 4-hydroxy-4-(6-hexyloxynaphth-2-yl)piperidine, 0.353 gm (56%) of the title compound were recovered as a white solid by the procedure described in Example 9.

MS(FD): m/e=516 (M+1); EA: Calculated for $C_{32}H_{40}N_2O_4$: C, 74.39; H, 7.80; N, 5.42. Found: C, 74.59; H, 7.98; N, 5.51.

EXAMPLE 17

(2S)-(−)-1-(4-indolyloxy)-3-[4-hydroxy-4-(6-benzyloxynaphth-2-yl)piperidine-1-yl]-2-propanol Beginning with 0.170 gm (0.90 mmol) (S)-(+)-4-(oxiranylmethoxy)-1H-indole and 0.300 gm (0.90 mMol) 4-hydroxy-4-(6-benzyloxynaphth-2-yl)piperidine, 0.388 gm (83%) of the title compound were recovered as a white solid by the procedure described in Example 9.

MS(FD): m/e=522 (M$^+$); EA: Calculated for $C_{33}H_{34}N_2O_4$: C, 75.24; H, 6.56; N, 5.36. Found: C, 75.56; H, 6.43; N, 5.31.

EXAMPLE 18

(2S)-(−)-1-(4-indolyloxy)-3-[4-hydroxy-4-(6-phenethyloxynaphth-2-yl)piperidine-1-yl]-2-propanol oxalate Beginning with 0.109 gm (0.60 mMol) (S)-(+)-4-(oxiranylmethoxy)-1H-indole and 0.200 gm (0.60 mMol) 4-hydroxy-4-(6-phenethyloxynaphth-2-yl)piperidine, 0.202 gm (67%) (2S)-(−)-1-(4-indolyloxy)-3-[4-hydroxy-4-(6-phenethyloxynaphth-2-yl)piperidine-1-yl]-2-propanol were recovered by the procedure described in Example 9. The oxalate salt was prepared to provide the title compound.

MS(FD): m/e=536 (M$^+$)

EXAMPLE 19

(2S)-(−)-1-(4-indolyloxy)-3-[4-hydroxy-4-(7-methoxynaphth-2-yl)piperidine-1-yl]-2-propanol Beginning with 0.334 gm (1.77 mMol) (S)-(+)-4-(oxiranylmethoxy)-1H-indole and 0.455 gm (1.77 mMol) of 4-hydroxy-4-(7-methoxynaphth-2-yl)piperidine, 0.570 gm (72%) of the title compound was recovered as a white solid by the procedure described in Example 9.

MS(FD): m/e=446(M$^+$)

Serotonin $1_A$ receptor activity

The compounds of the present invention are active at the serotonin $1_A$ receptor, particularly as antagonists and as partial agonists at that receptor, and are distinguished by their selectivity. Previously known compounds with that activity typically have the disadvantage of possessing other non-serotonin related central nervous system activities as well. It is now well understood by pharmacologists and physicians that pharmaceuticals which have a single physiological activity, or which are much more active in the desired activity than in their other activities, are much more desirable for therapy than are compounds which have multiple activities at about the same dose.

Many other serotonin $1_A$ receptor antagonists typically have α-adrenergic or β-adrenergic activity as well, and are therefore nonselective for 5HT-$1_A$ activity.

The 5HT-$1_A$ receptor binding potency of the present compounds has been measured by a modification of the binding assay described by Taylor, et al. (*J. Pharmacol. Exp. Ther.* 236, 118–125, 1986); and Wong, et al., *Pharm. Biochem. Behav.* 46, 173–77 (1993). Membranes for the binding assay were prepared from male Sprague-Dawley rats (150–250 g). The animals were killed by decapitation, and the brains were rapidly chilled and dissected to obtain the hippocampi. Membranes from the hippocampi were either prepared that day, or the hippocampi were stored frozen (−70°) until the day of preparation. The membranes were prepared by homogenizing the tissue in 40 volumes of ice-cold Tris-HCl buffer (50 mM, pH 7.4 at 22°) using a homogenizer for 15 sec., and the homogenate was centrifuged at 39800×g for 10 min. The resulting pellet was then resuspended in the same buffer, and the centrifugation and resuspension process was repeated three additional times to wash the membranes. Between the second and third washes the resuspended membranes were incubated for 10 min. at 37° to facilitate the removal of endogenous ligands. The final pellet was resuspended in 67 mM Tris-HCl, pH 7.4, to a concentration of 2 mg of tissue original wet weight/200 μl. This homogenate was stored frozen (−70°) until the day of the binding assay. Each tube for the binding assay had a final volume of 800 μl and contained the following: Tris-HCl (50 mM), pargyline (10 μM), CaCl$_2$ (3 mM), [$^3$H]8-OH-DPAT (1.0 nM), appropriate dilutions of the drugs of interest, and membrane resuspension equivalent to 2 mg of original tissue wet weight, for a final pH of 7.4. The assay tubes were incubated for either 10 min. or 15 min. at 37°, and the contents were then rapidly filtered through GF/B filters (pretreated with 0.5% polyethyleneimine), followed by four one-ml washes with ice-cold buffer. The radioactivity trapped by the filters was quantitated by liquid scintillation spectrometry, and specific [$^3$H]8-OH-DPAT binding to the 5-HT$_{1A}$ sites was defined as the difference between [$^3$H]8-OH-DPAT bound in the presence and absence of 10 μM 5-HT.

IC$_{50}$ values, i.e., the concentration required to inhibit 50% of the binding, were determined from 12-point competition curves using nonlinear regression (SYSTAT, SYSTAT, Inc., Evanston, Ill.).

Additional binding assays of some of the present compounds have been carried out by an assay method which uses a cloned cell line which expresses the serotonin $1_A$ receptor, rather than the hippocampal membranes. Such cloned cell lines have been described by Fargin, et al., *J.Bio. Chem.*, 264, 14848–14852 (1989), Aune, et al., *J. Immunology*, 151, 1175–1183 (1993), and Raymond, et al.,*Naunyn-Schmiedeberg's Arch. Pharmacol.*, 346, 127–137 (1992). Results from the cell line assay are substantially in agreement with results from the hippocampal membrane assay.

The efficacy of the compounds of the invention to inhibit the reuptake of serotonin has been determined by a paroxetine binding assay, the usefulness of which is set out by Wong, et al., *Neuropsychopharmacology*, 8, 23–33 (1993). Synaptosomal preparations from rat cerebral cortex were made from the brains of 100–150 g Sprague-Dawley rats which were killed by decapitation. The cerebral cortex was homogenized in 9 volumes of a medium containing 0.32 M sucrose and 20 μM glucose. The preparations were resuspended after centrifugation by homogenizing in 50 volumes of cold reaction medium (50 μM sodium chloride, 50 μM potassium chloride, pH 7.4) and centrifuging at 50,000 g for 10 minutes. The process was repeated two times with a 10-minute incubation at 37° C. between the second and third washes. The resulting pellet was stored at −70° C. until use. Binding of $^3$H-paroxetine to 5-HT uptake sites was carried out in 2 ml reaction medium containing the appropriate drug concentration, 0.1 nM $^3$H-paroxetine, and the cerebral cortical membrane (50 μg protein/tube). Samples were incubated at 37° C. for 30 minutes; those containing 1 μM fluoxetine were used to determine nonspecific binding of $^3$H-paroxetine. After incubation, the tubes were filtered through Whatman GF/B filters, which were soaked in 0.05% polyethyleneimine for 1 hour before use, using a cell harvester by adding about 4 ml cold Tris buffer (pH 7.4), aspirating, and rinsing the tubes three additional times. Filters were then placed in scintillation vials containing 10 ml scintillation fluid, and the radioactivity was measured by liquid scintillation spectrophotometry.

Results of testing representative compounds of the invention by the above method showed potent reuptake activity, in many cases activity in the low nM range.

The pharmacological activities which have been described immediately above provide the mechanistic basis for the pharmaceutical utility of the compounds described in this document. A number of pharmaceutical utilities will be described below.

Throughout this document, the person or animal to be treated will be described as the "subject", and it will be understood that the most preferred subject is a human. However, it must be noted that the study of adverse conditions of the central nervous system in non-human animals is only now beginning, and that some instances of such treatments are coming into use. For example, fluoxetine, and perhaps other serotonin reuptake inhibitors, are being used in companion animals such as dogs for the treatment of behavioral problems and the like. Accordingly, use of the present compounds in non-human animals is contemplated. It will be understood that the dosage ranges for other animals will necessarily be quite different from the doses administered to humans, and accordingly that the dosage ranges described below in the section on tobacco withdrawal must be recalculated. For example, a small dog may be only ⅒th of a typical human's size, and it will therefore be necessary for a much smaller dose to be used. The determination of an effective amount for a certain non-human animal is carried out in the same manner described below in the case of humans, and veterinarians are well accustomed to such determinations.

The activity of the compounds at the serotonin $1_A$ receptor provides a method of affecting the serotonin $1_A$ receptor which comprises administering to a subject in need of such treatment an effective amount of a compound of Formula I. Reasons for the necessity of affecting the $1_A$ receptor will be described in detail below, but in all cases the effect on the serotonin $1^A$ receptor is brought about through the compounds' potency as antagonists or partial agonists at that receptor. A subject in need of a modification of the effects of the 5HT-$1_A$ receptor is one having one or more of the specific conditions and problems to be further described, or a condition or problem not yet recognized as created by an imbalance or malfunction of the 5HT-$1_A$ receptor, since research on the central nervous system is presently ongoing in many fields and newly discovered relationships between receptors and therapeutic needs are continually being discovered. In all cases, however, it is the compounds' ability to affect the serotonin $1_A$ receptor which creates their physiological or therapeutic effects.

An effective amount of a compound for affecting the serotonin $1_A$ receptor is the amount, or dose, of the compound which provides the desired effect in the subject under diagnosis or treatment. The amount is an individualized determination, and physicians are well accustomed to adjusting effective amounts of pharmaceuticals based on observations of the subject. The effective amount of the present compounds is discussed in some detail below, in the discussion about the treatment of tobacco withdrawal symptoms, and that discussion is applicable to the determination of the effective amount in all treatment methods.

Further, the activity of compounds of Formula I in the inhibition of the reuptake of serotonin provides a method of inhibiting the reuptake of serotonin comprising administering to a subject in need of such treatment an effective amount of a compound of that formula. It is now known that numerous physiological and therapeutic benefits are obtained through the administration of drugs which inhibit the reuptake of serotonin. The treatment of depression with drugs of the class of which fluoxetine is the leader has become perhaps the greatest medical breakthrough of the past decade. Numerous other treatment methods carried out by the administration of the compounds of Formula XIII will be set out in detail below. Again, the effective amount of a compound for the inhibition of serotonin reuptake, or for a specific therapeutic method which depends on the inhibition of reuptake, is determined in the manner described below under the heading of smoking withdrawal.

The unique combination of 5HT-$1_A$ receptor activity and serotonin reuptake inhibition possessed by the compounds of the invention afford a method of providing to a subject both physiological activities with a single administration of a compound of that formula. As discussed in the Background section of this document, the value of combining the two effects has been discussed in the literature, and it is believed that the present compounds are advantageous in that they provide both physiological effects in a single drug while causing only a low degree of chromosomal aberrations in the subject. It is presently believed that the result of administration of a compound of Formula I is to provide physiological and therapeutic treatment methods which are typical of those provided by presently known serotonin reuptake inhibitors, but with enhanced efficacy and quicker onset of action. In addition, of course, all of the physiological and therapeutic methods provided by compounds which affect the serotonin $1_A$ receptor are provided by the compounds of Formula I as well.

The activities of Formula I compounds at the 5HT-$1_A$ receptor and in reuptake inhibition are of comparable potencies, so a single effective amount is effective for both purposes.

Further discussion of specific therapeutic methods provided by the dual activity compounds of Formula I, and the diseases and conditions advantageously treated therewith, will be provided below.

Tobacco or nicotine withdrawal

It is well known that the chronic administration of nicotine results in tolerance and, eventually, dependence. The use of tobacco has become extremely widespread in all countries, despite the well known adverse effects of the use of tobacco in all its forms. Thus, it is clear that tobacco use is extremely habit-forming, if not addictive, and that its use provides sensations to the user which are pleasant and welcome, even though the user may be fully aware of the drastic long term ill effects of its use.

Rather recently, vigorous campaigns against the use of tobacco have taken place, and it is now common knowledge that the cessation of smoking brings with it numerous unpleasant withdrawal symptoms, which include irritability, anxiety, restlessness, lack of concentration, lightheadedness, insomnia, tremor, increased hunger and weight gain, and, of course, a craving for tobacco.

At the present time, probably the most widely used therapy to assist the cessation of tobacco use is nicotine replacement, by the use of nicotine chewing gum or nicotine-providing transdermal patches. It is widely known, however, that nicotine replacement is less effective without habit-modifying psychological treatment and training.

Thus, the present method of preventing or alleviating the symptoms caused by withdrawal or partial withdrawal from the use of tobacco or of nicotine comprises the previously discussed method of affecting the serotonin $1_A$ receptor, in that the treatment method comprises the administration of an effective amount of one of the serotonin $1_A$ receptor-active compounds of Formula I to the subject. The method of the present invention is broadly useful in assisting persons who want to cease or reduce their use of tobacco or nicotine. Most commonly, the form of tobacco use is smoking, most commonly the smoking of cigarettes. The present invention is also helpful, however, in assisting in breaking the habit of all types of tobacco smoking, as well as the use of snuff, chewing tobacco, etc. The present method is also helpful to those who have replaced, or partially replaced, their use of tobacco with the use of nicotine replacement therapy. Thus, such subjects can be assisted to reduce and even eliminate entirely their dependence on nicotine in all forms.

A particular benefit of therapy with the present compounds is the elimination or reduction of the weight gain which very often results from reducing or withdrawing from use of tobacco or nicotine.

It will be understood that the present invention is useful for preventing or alleviating the withdrawal symptoms which afflict subjects who are trying to eliminate or reduce their use of tobacco or nicotine. The common withdrawal symptoms of such people include, at least, irritability, anxiety, restlessness, lack of concentration, insomnia, nervous tremor, increased hunger and weight gain, lightheadedness, and the craving for tobacco or nicotine. The prevention or alleviation of such symptoms, when they are caused by or occur in conjunction with ceasing or reducing the subject's use of tobacco or nicotine is a desired result of the present invention and an important aspect of it.

The invention is carried out by administering an effective amount of a compound of Formula I to a subject who is in need of or carrying out a reduction or cessation of tobacco or nicotine use.

The effective amount of compound to be administered, in general, is from about 1 to about 100 mg/day; as usual, the daily dose may be administered in a single bolus, or in divided doses, depending on the judgment of the physician in charge of the case. A more preferred range of doses is from about 5 to about 100 mg/day; other dosage ranges which may be preferred in certain circumstances are from about 10 to about 50 mg/day; from about 5 to about 50 mg/day; from about 10 to about 25 mg/day; and a particularly preferred range is from about 20 to about 25 mg/day. It will be understood that the effective amount for a given subject is always to be set by the judgment of the attending physician, and that the dose is subject to modification based on the size of the subject, the lean or fat nature of the subject, the characteristics of the particular compound chosen, the intensity of the subject's tobacco habit, the intensity of the subject's withdrawal symptoms, and psychological factors which may affect the subject's physiological responses. Thus, the effective amount is the amount required to prevent or alleviate the symptoms of withdrawal or partial withdrawal in the subject under treatment.

The effect of compounds in alleviating the symptoms of nicotine withdrawal is evaluated in rats by an auditory startle test, which is carried out as follows.

Procedures for Nicotine Withdrawal Studies

Animals: Male Long Evans rats were individually housed in a controlled environment on a 12 hour light-dark cycle and were given free access to food (Purina Rodent Chow) and water. All treatment groups contained 8–10 rats.

Chronic Nicotine Treatment: Rats were anesthetized with halothane and Alzet osmotic minipumps (Alza Corporation, Palo Alto, Calif., Model 2ML2) were implanted subcutaneously. Nicotine ditartrate was dissolved in physiological saline. Pumps were filled with either nicotine ditartrate (6 mg/kg base/day) or physiological saline. Twelve days following implantation of pumps, rats were anesthetized with halothane and the pumps were removed.

Auditory Startle Respose: The sensory motor reactions [auditory startle response (peak amplitude Vmax)] of individual rats was recorded using San Diego Instruments startle chambers (San Diego, Calif.). Startle sessions consisted of a 5-minute adaptation period at a background noise level of 70±3 dBA immediately followed by 25 presentations of auditory stimuli (120±2 dBA noise, 50 ms duration) presented at 8-second intervals. Peak startle amplitudes were then averaged for all 25 presentations of stimuli for each session. Auditory startle responding was evaluated daily at 24 hour intervals on days 1–4 following nicotine withdrawal.

The invention also provides pharmaceutical compositions which comprise a compound of Formula I, and a method of treating a pathological condition which is created by or is dependent upon decreased availability of serotonin, dopamine or norepinephrine, which method comprises administering the same adjunctive therapy to a subject in need of such treatment.

It will be understood that, while the compounds of Formula I individually provide the benefit of the combination of serotonin reuptake inhibitors and serotonin 1A antagonists, it is entirely possible to administer a compound of Formula I in combination with a conventional serotonin reuptake inhibitor in order to obtain still further enhanced results in potentiating serotonin reuptake inhibition.

Fluoxetine, N-methyl-3-(p-trifluoromethylphenoxy)-3-phenylpropylamine, is marketed in the hydrochloride salt form, and as the racemic mixture of its two enantiomers. U.S. Pat. No. 4,314,081 is an early reference on the compound. Robertson, et al., *J. Med. Chem.* 31, 1412 (1988), taught the separation of the R and S enantiomers of fluoxetine and showed that their activity as serotonin uptake inhibitors is similar to each other. In this document, the word "fluoxetine" will be used to mean any acid addition salt or the free base, and to include either the racemic mixture or either of the R and S enantiomers.

Duloxetine, N-methyl-3-(1-naphthalenyloxy)-3-(2-thienyl)propanamine, is usually administered as the hydrochloride salt and as the (+) enantiomer. It was first taught by U.S. Pat. No. 4,956,388, which shows its high potency. The word "duloxetine" will be used here to refer to any acid addition salt or the free base of the molecule.

Venlafaxine is known in the literature, and its method of synthesis and its activity as an inhibitor of serotonin and norepinephrine uptake are taught by U.S. Pat. No. 4,761,501. Venlafaxine is identified as compound A in that patent.

Milnacipran (N,N-diethyl-2-aminomethyl-1-phenylcyclopropanecarboxamide) is taught by U.S. Pat. No. 4,478,836, which prepared milnacipran as its Example 4. The patent describes its compounds as antidepressants. Moret, et al., *Neuropharmacolgy* 24, 1211–19 (1985), describe its pharmacological activities.

Citalopram, 1-[3-(dimethylamino)propyl]-1-(4-fluorophenyl) -1,3-dihydro-5-isobenzofurancarbonitrile, is disclosed in U.S. Pat. No. 4,136,193 as a serotonin reuptake inhibitor. Its pharmacology was disclosed by Christensen, et al., *Eur. J. Pharmacol.* 41, 153 (1977), and reports of its clinical effectiveness in depression may be found in Dufour, et al., *Int. Clin. Psychopharmacol.* 2, 225 (1987), and Timmerman, et al., ibid., 239.

Fluvoxamine, 5-methoxy-1-[4-(trifluoromethyl)phenyl]-1-pentanone 0-(2-aminoethyl)oxime, is taught by U.S. Pat. No. 4,085,225. Scientific articles about the drug have been published by Claassen, et al., *Brit. J. Pharmacol.* 60, 505 (1977); and De Wilde, et al., *J. Affective Disord.* 4, 249 (1982); and Benfield, et al., *Drugs* 32, 313 (1986).

Sertraline, 1-(3,4-dichlorophenyl)-4-methylaminotetralin, is disclosed in U.S. Pat. No. 4,536,518.

Paroxetine, trans-(−)-3-[(1,3-benzodioxol-5-yloxy) methyl]-4-(4-fluorophenyl)piperidine, may be found in U.S. Pat. Nos. 3,912,743 and 4,007,196. Reports of the drug's activity are in Lassen, *Eur. J. Pharmacol.* 47, 351 (1978); Hassan, et al., *Brit. J. Clin. Pharmacol.* 19, 705 (1985); Laursen, et al., *Acta Psychiat. Scand.* 71, 249 (1985); and Battegay, et al., *Neuropsychobiology* 13, 31 (1985).

All of the U.S. patents which have been mentioned above in connection with compounds used in the present invention are incorporated herein by reference.

In general, combinations and methods of treatment using fluoxetine or duloxetine as the SRI are preferred.

It will be understood by the skilled reader that all of the compounds used in the present invention are capable of forming salts, and that the salt forms of pharmaceuticals are commonly used, often because they are more readily crystallized and purified than are the free bases. In all cases, the use of the pharmaceuticals described above as salts is contemplated in the description herein, and often is preferred, and the pharmaceutically acceptable salts of all of the compounds are included in the names of them.

The dosages of the drugs used in the present combination must, in the final analysis, be set by the physician in charge of the case, using knowledge of the drugs, the properties of the drugs in combination as determined in clinical trials, and the characteristics of the subject, including diseases other than that for which the physician is treating the subject. General outlines of the dosages, and some preferred human dosages, can and will be provided here. Dosage guidelines for some of the drugs will first be given separately; in order to create a guideline for any desired combination, one would choose the guidelines for each of the component drugs.

Fluoxetine: from about 1 to about 80 mg, once/day; preferred, from about 10 to about 40 mg once/day; preferred for bulimia and obsessive-compulsive disease, from about 20 to about 80 mg once/day;

Duloxetine: from about 1 to about 30 mg once/day; preferred, from about 5 to about 20 mg once/day;

Venlafaxine: from about 10 to about 150 mg once-thrice/day; preferred, from about 25 to about 125 mg thrice/day;

Milnacipran: from about 10 to about 100 mg once-twice/day; preferred, from about 25 to about 50 mg twice/day;

Citalopram: from about 5 to about 50 mg once/day; preferred, from about 10 to about 30 mg once/day;

Fluvoxamine: from about 20 to about 500 mg once/day; preferred, from about 50 to about 300 mg once/day;

Paroxetine: from about 5 to about 100 mg once/day; preferred, from about 50 to about 300 mg once/day.

In more general terms, one would create a combination of the present invention by choosing a dosage of SRI according to the spirit of the above guideline, and choosing a dosage of the compound of Formula I in the ranges taught above.

Preferred pathological conditions to be treated by the present treatment methods include depression, bulimia, obsessive-compulsive disease and obesity. Another preferred condition more specific to combinations including preferably duloxetine but also venlafaxine and milnacipran is urinary incontinence.

Depression in its many variations has recently become much more visible to the general public than it has previously been. It is now recognized as an extremely damaging disorder, and one that afflicts a surprisingly large fraction of the human population. Suicide is the most extreme symptom of depression, but millions of people, not quite so drastically afflicted, live in misery and partial or complete uselessness, and afflict their families as well by their affliction. The introduction of fluoxetine was a breakthrough in the treatment of depression, and depressives are now much more likely to be diagnosed and treated than they were only a decade ago. Duloxetine is in clinical trials for the treatment of depression and is likely to become a marketed drug for the purpose.

Depression is often associated with other diseases and conditions, or caused by such other conditions. For example, it is associated with Parkinson's disease; with HIV; with Alzheimer's disease; and with abuse of anabolic steroids. Depression may also be associated with abuse of any substance, or may be associated with behavioral problems resulting from or occurring in combination with head injuries, mental retardation or stroke. Depression in all its variations is a preferred target of treatment with the present adjunctive therapy method and compositions.

Obsessive-compulsive disease appears in a great variety of degrees and symptoms, generally linked by the victim's uncontrollable urge to perform needless, ritualistic acts. Acts of acquiring, ordering, cleansing and the like, beyond any rational need or rationale, are the outward characteristic of the disease. A badly afflicted subject may be unable to do anything but carry out the rituals required by the disease. Fluoxetine is approved in the United States and other countries for the treatment of obsessive-compulsive disease and has been found to be effective.

Obesity is a frequent condition in the American population. It has been found that fluoxetine will enable an obese subject to lose weight, with the resulting benefit to the circulation and heart condition, as well as general well being and energy.

Urinary incontinence is classified generally as stress or urge incontinence, depending on whether its root cause is the inability of the sphincter muscles to keep control, or the overactivity of the bladder muscles. Duloxetine controls both types of incontinence, or both types at once, and so is important to the many who suffer from this embarrassing and disabling disorder.

The present treatment methods are useful for treating many other diseases, disorders and conditions as well, as set out below. In many cases, the diseases to be mentioned here are classified in the International Classification of Diseases, 9th Edition (ICD), or in the Diagnostic and Statistical Manual of Mental Disorders, 3rd Version Revised, published by the American Psychiatric Association (DSM). In such cases, the ICD or DSM code numbers are supplied below for the convenience of the reader.

depression, ICD 296.2 & 296.3, DSM 296, 294.80, 293.81, 293.82, 293.83, 310.10, 318.00, 317.00 migraine pain, particularly neuropathic pain bulimia, ICD 307.51, DSM 307.51 premenstrual syndrome or late luteal phase syndrome, DSM 307.90 alcoholism, ICD 305.0, DSM 305.00 & 303.90 tobacco abuse, ICD 305.1, DSM 305.10 & 292.00 panic disorder, ICD 300.01, DSM 300.01 & 300.21 anxiety, ICD 300.02, DSM 300.00 post-traumatic syndrome, DSM 309.89 memory loss, DSM 294.00 dementia of aging, ICD 290 social phobia, ICD 300.23, DSM 300.23 attention deficit hyperactivity disorder, ICD 314.0 disruptive behavior disorders, ICD 312 impulse control disorders, ICD 312, DSM 312.39 & 312.34 borderline personality disorder, ICD 301.83, DSM 301.83 chronic fatigue syndrome premature ejaculation, DSM 302.75 erectile difficulty, DSM 302.72 anorexia nervosa, ICD 307.1, DSM 307.10 disorders of sleep, ICD 307.4 autism mutism trichotillomania

Further, the compounds of Formula I are useful for alleviating the symptoms of smoking cessation or nicotine withdrawal when administered alone or in combination with a serotonin reuptake inhibitor. The SRI's to be used in this treatment method, and the administration methods and formulations, are as described above. The use of the present compounds with SRI's in subjects striving to stop use of tobacco or nicotine provides surprisingly complete alleviation of the usual painful and damaging symptoms of such subjects, including nervousness, irritability, craving, excessive appetite, anxiety, depression in many forms, inability to concentrate, and the like. Thus, the control or elimination of weight gain in the subject undergoing withdrawal from or reduction of tobacco or nicotine use is a particularly valuable and preferred benefit of the use of a present compound in combination with an SRI.

Therapeutic applications

The compounds of Formula I are useful for other important therapeutic purposes, as well as in combination with SRIs and in nicotine withdrawal or smoking cessation cases. In particular, the compounds are valuable for binding, blocking or modulating the serotonin $1_A$ receptor, and for the treatment or prophylaxis of conditions caused by or influenced by defective function of that receptor. In particular, the compounds are useful for antagonism at the serotonin $1_A$ receptor and accordingly are used for the treatment or prevention of conditions caused by or affected by excessive activity of that receptor.

More particularly, the compounds are useful in the treatment of anxiety, depression, hypertension, cognitive disorders, psychosis, sleep disorders, gastric motility disorders, sexual dysfunction, brain trauma, memory loss, appetite disorders and obesity, substance abuse, obsessive-compulsive disease, panic disorder and migraine.

Anxiety and its frequent concomitant, panic disorder, may be particularly mentioned in connection with the present compounds. The subject is carefully explained by the Diagnostic and Statistical Manual of Mental Disorders, published by the American Psychiatric Association, which classifies anxiety under its category 300.02. A further particularly noted disorder is depression and the group of depression-related disorders, which are discussed above in the discussion of adjunctive therapy with SRIs.

The unique combination of pharmacological properties possessed by the compounds of Formula I permit those compounds to be used in a method of simultaneously treating anxiety and depression. The anxiety portion of the combined syndrome is believed to be attacked by the 5HT-$1_A$ receptor-affecting property of the compounds, and the depression portion of the condition is believed to be addressed by the reuptake inhibition property. Thus, administration of an effective amount, as discussed above, of a compound of Formula I will provide treatment for the combined condition.

Pharmaceutical compositions

It is customary to formulate pharmaceuticals for administration, to provide control of the dosage and stability of the product in shipment and storage, and the usual methods of formulation are entirely applicable to the compounds of Formula I. Such compositions, comprising at least one pharmaceutically acceptable carrier, are valuable and novel because of the presence of the compounds of Formula I therein. Although pharmaceutical chemists are well aware of many effective ways to formulate pharmaceuticals, which technology is applicable to the present compounds, some discussion of the subject will be given here for the convenience of the reader.

The usual methods of formulation used in pharmaceutical science and the usual types of compositions may be used, including tablets, chewable tablets, capsules, solutions, parenteral solutions, intranasal sprays or powders, troches, suppositories, transdermal patches and suspensions. In general, compositions contain from about 0.5% to about 50% of the compound in total, depending on the desired dose and the type of composition to be used. The amount of the compound, however, is best defined as the effective amount, that is, the amount of each compound which provides the desired dose to the subject in need of such treatment. The activity of the compounds do not depend on the nature of the composition, so the compositions are chosen and formulated solely for convenience and economy. Any compound may be formulated in any desired form of composition. Some discussion of different compositions will be provided, followed by some typical formulations.

Capsules are prepared by mixing the compound with a suitable diluent and filling the proper amount of the mixture in capsules. The usual diluents include inert powdered substances such as starch of many different kinds, powdered cellulose, especially crystalline and microcrystalline cellulose, sugars such as fructose, mannitol and sucrose, grain flours and similar edible powders.

Tablets are prepared by direct compression, by wet granulation, or by dry granulation. Their formulations usually incorporate diluents, binders, lubricants and disintegrators as well as the compound. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders are substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders.

A lubricant is necessary in a tablet formulation to prevent the tablet and punches from sticking in the die. The lubricant is chosen from such slippery solids as talc, magnesium and calcium stearate, stearic acid and hydrogenated vegetable oils.

Tablet disintegrators are substances which swell when wetted to break up the tablet and release the compound. They include starches, clays, celluloses, algins and gums. More particularly, corn and potato starches, methylcellulose, agar, bentonite, wood cellulose, powdered natural sponge, cation-exchange resins, alginic acid, guar gum, citrus pulp and carboxymethylcellulose, for example, may be used, as well as sodium lauryl sulfate.

Enteric formulations are often used to protect an active ingredient from the strongly acidic contents of the stomach. Such formulations are created by coating a solid dosage form with a film of a polymer which is insoluble in acidic environments, and soluble in basic environments. Exemplary films are cellulose acetate phthalate, polyvinyl acetate phthalate, hydroxypropyl methylcellulose phthalate and hydroxypropyl methylcellulose acetate succinate.

Tablets are often coated with sugar as a flavor and sealant, or with film-forming protecting agents to modify the dissolution properties of the tablet. The compounds may also be formulated as chewable tablets, by using large amounts of pleasant-tasting substances such as mannitol in the formulation, as is now well-established practice. Instantly dissolving tablet-like formulations are also now frequently used to assure that the subject consumes the dosage form, and to avoid the difficulty in swallowing solid objects that bothers some subjects.

When it is desired to administer the combination as a suppository, the usual bases may be used. Cocoa butter is a traditional suppository base, which may be modified by addition of waxes to raise its melting point slightly. Water-miscible suppository bases comprising, particularly, polyethylene glycols of various molecular weights are in wide use, also.

Transdermal patches have become popular recently. Typically they comprise a resinous composition in which the drugs will dissolve, or partially dissolve, which is held in contact with the skin by a film which protects the composition. Many patents have appeared in the field recently. Other, more complicated patch compositions are also in use, particularly those having a membrane pierced with pores through which the drugs are pumped by osmotic action.

The following typical formulae are provided for the interest and information of the pharmaceutical scientist.

Formulation 1

Hard gelatin capsules are prepared using the following ingredients:

|  | Quantity (mg/capsule) |
|---|---|
| Example 10 | 20 mg |
| Starch, dried | 200 mg |
| Magnesium stearate | 10 mg |
| Total | 230 mg |

We claim:

1. A compound which is (2S)-(−)-1-(4-indolyloxy)-3-[4-hydroxy-4-(naphth-2-yl)piperidin-1-yl]-2-propanol, or pharmaceutically acceptable salts thereof.

2. A pharmaceutical composition comprising a pharmaceutically acceptable carrier or excipient and a compound of claim 1.

3. A method of treating depression which comprises administering to a subject in need of such treatment an effective amount of a compound which is (2S)-(−)-1-(4-indolyloxy)-3-[4-hydroxy-4-(naphth-2-yl)piperidin-1-yl]-2-propanol, or pharmaceutically acceptable salts thereof.

4. A method of treating anxiety which comprises administering to a subject in need of such treatment an effective amount of a compound which is (2S)-(−)-1-(4-indolyloxy)-3-[4-hydroxy-4-(naphth-2-yl)piperidin-1-yl]-2-propanol, or pharmaceutically acceptable salts thereof.

5. A method of treating anxiety and depression which comprises administering to a subject in need of such treatment an effective amount of a compound which is (2S)-(−)-1-(4-indolyloxy)-3-[4-hydroxy-4-(naphth-2-yl)piperidin-1-yl]-2-propanol, or pharmaceutically acceptable salts thereof.

* * * * *